(12) United States Patent
Kim (10) Patent No.: US 7,800,494 B2
(45) Date of Patent: Sep. 21, 2010

(54) METHOD AND APPARATUS FOR WIRELESSLY RECEIVING BIOLOGICAL SIGNAL

(75) Inventor: Jong-pal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 362 days.

(21) Appl. No.: 12/056,319

(22) Filed: Mar. 27, 2008

(65) Prior Publication Data

US 2009/0160642 A1 Jun. 25, 2009

(30) Foreign Application Priority Data

Dec. 21, 2007 (KR) .................. 10-2007-0135241

(51) Int. Cl.
*G08B 1/08* (2006.01)
*G08B 23/00* (2006.01)
*A61B 5/00* (2006.01)

(52) U.S. Cl. .................. 340/539.12; 340/539.3; 340/573.1; 340/309.16; 600/300; 600/301; 128/903; 702/19

(58) Field of Classification Search ............. 340/539.12
See application file for complete search history.

(56) References Cited

U.S. PATENT DOCUMENTS 6,577,901 B2 * 6/2003 Thompson .................. 607/60
6,671,552 B2 * 12/2003 Merritt et al. ................ 607/29

* cited by examiner

*Primary Examiner*—Donnie L Crosland
(74) *Attorney, Agent, or Firm*—Sughrue Mion, PLLC (57) ABSTRACT

A method of wirelessly receiving a biological signal is provided. Thus, it is possible to considerably reduce power consumption of a wireless biological signal receiver by determining a transmission period of an externally received biological signal, setting an operation mode of the wireless biological signal receiver to an active mode in which it is possible to receive the biological signal for a predetermined time for each determined transmission period and receiving the biological signal, and changing the operation mode from the active mode to a low-power mode in which it is impossible to receive the biological signal, after the predetermined time is elapsed with respect to each determined transmission period.

18 Claims, 5 Drawing Sheets

METHOD AND APPARATUS FOR WIRELESSLY RECEIVING BIOLOGICAL SIGNAL

CROSS-REFERENCE TO RELATED PATENT APPLICATION

This application claims the benefit of Korean Patent Application No. 10-2007-0135241, filed on Dec. 21, 2007, in the Korean Intellectual Property Office, the disclosure of which is incorporated herein in its entirety by reference.

BACKGROUND

1. Field

One or more embodiments of the present invention relate to a method, medium, and apparatus for wirelessly receiving a biological signal, and more particularly, to a method, medium, and apparatus for wirelessly receiving a biological signal by using a wireless system for transmitting and receiving a biological signal.

2. Description of the Related Art

In general, biological signals represent brain waves, blood pressure, a pulse, body temperature, and the like. Such biological signals are essential in medicine in terms of providing a possible cure or an accurate diagnosis. In addition, the medical expenses for the elderly and chronics in the future are likely to increase since it is expected that their number will increase.

Accordingly, in order to continuously monitor patients and check their health condition, medical devices that allow the patients themselves to monitor their health condition are actively being researched. As a typical example, a person, who would like to assess their health, can do so by wearing an apparatus for measuring biological signals, and thus, immediately check their health condition. Accordingly, such apparatus can provide services such as health examinations and services in case of emergency.

SUMMARY

One or more embodiments of the present invention provide a method and apparatus for wirelessly receiving a biological signal so as to be capable of reducing power consumption of a wireless biological signal receiver, and a computer-readable medium having a computer readable code to implement the method of wirelessly receiving a biological signal.

One or more embodiments of the present invention also provide a method of wirelessly receiving data so as to be capable of reducing power consumption of a wireless data receiver, and a computer-readable medium having a computer readable code to implement the method of wirelessly receiving data.

Additional aspects and/or advantages will be set forth in part in the description which follows and, in part, will be apparent from the description, or may be learned by practice of the invention.

According to an aspect of the present invention, there is provided a method of receiving a biological signal by using a wireless biological signal receiver, the method including: determining a transmission period of an externally received biological signal; setting an operation mode of the wireless biological signal receiver to an active mode in which it is possible to receive the biological signal for a predetermined time for each determined transmission period and receiving the biological signal; and changing the operation mode from the active mode to a low-power mode in which it is impossible to receive the biological signal, after the predetermined time is elapsed with respect to each determined transmission period.

According to another aspect of the present invention, there is provided a computer-readable medium having a computer readable code to implement a method of wirelessly receiving a biological signal by using a wireless biological signal receiver, the method including: determining a transmission period of an externally received biological signal; setting an operation mode of the wireless biological signal receiver to an active mode in which it is possible to receive the biological signal for a predetermined time for each determined transmission period and receiving the biological signal; and changing the operation mode from the active mode to a low-power mode in which it is impossible to receive the biological signal, after the predetermined time is elapsed with respect to each determined transmission period.

According to another aspect of the present invention, there is provided a wireless biological signal receiver including: a transmission period determiner to determine a transmission period of an externally received biological signal; and an operation mode determiner to set an operation mode of the wireless biological signal receiver to an active mode in which it is possible to receive the biological signal for a predetermined time for each determined transmission period, receiving the biological signal, and changing the operation mode from the active mode to a low-power mode in which it is impossible to receive the biological signal, after the predetermined time is elapsed with respect to each determined transmission period.

According to another aspect of the present invention, there is provided a method of receiving wireless data by using a wireless data receiver, the method including: determining a transmission period of externally received data; setting an operation mode of the wireless data receiver to an active mode in which it is possible to receive the data for a predetermined time for each determined transmission period and receiving the data; and changing the operation mode from the active mode to a low-power mode in which it is impossible to receive the data, after the predetermined time is elapsed with respect to each determined transmission period.

According to another aspect of the present invention, there is provided a computer-readable medium having a computer readable code to implement a method of receiving wireless data by using a wireless data receiver, the method including: determining a transmission period of externally received data; setting an operation mode of the wireless data receiver to an active mode in which it is possible to receive the data for a predetermined time for each determined transmission period and receiving the data; and changing the operation mode from the active mode to a low-power mode in which it is impossible to receive the data, after the predetermined time is elapsed with respect to each determined transmission period.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION OF THE EMBODIMENTS

Reference will now be made in detail to embodiments, examples of which are illustrated in the accompanying drawings, wherein like reference numerals refer to the like elements throughout. In this regard, embodiments of the present invention may be embodied in many different forms and should not be construed as being limited to embodiments set forth herein. Accordingly, embodiments are merely described below, by referring to the figures, to explain aspects of the present invention.

Figure 1:
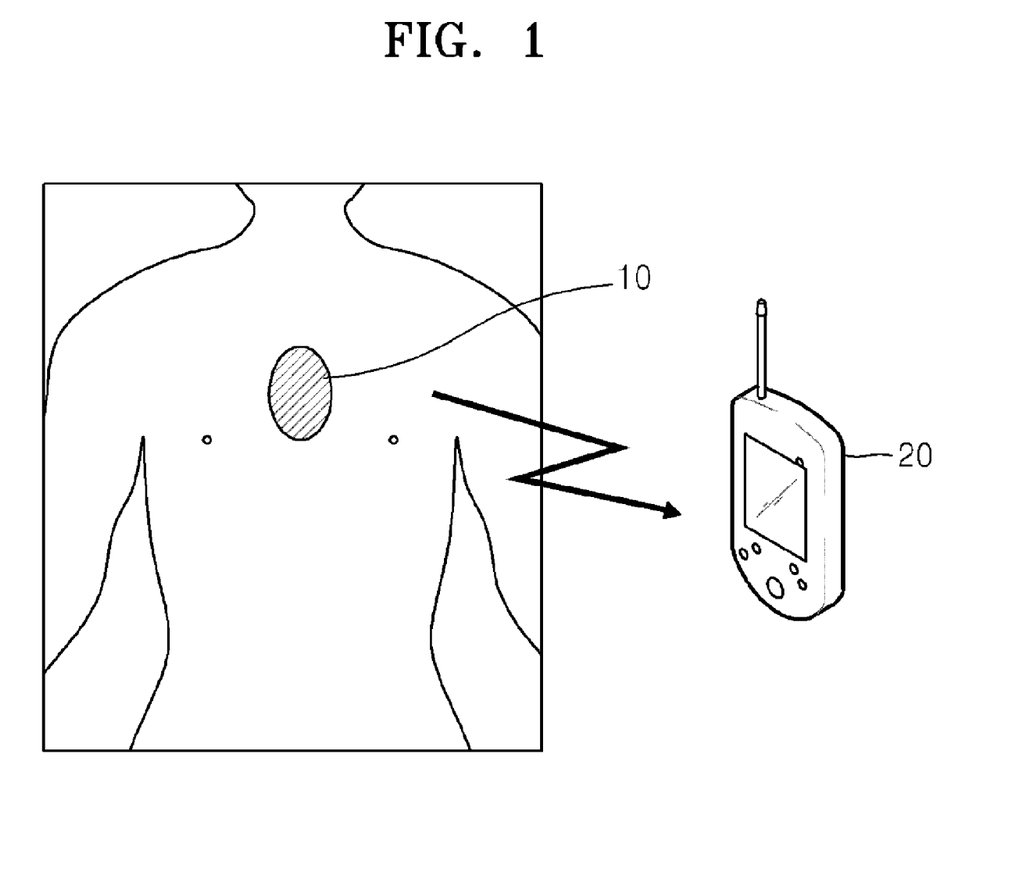
FIG. 1 illustrates an example of a wireless system for transmitting and receiving a biological signal, according to an embodiment of the present invention.

FIG. 1 illustrates an example of a wireless system for transmitting and receiving a biological signal, according to an embodiment of the present invention.

Referring to FIG. 1, the wireless system for transmitting and receiving the biological signal may include a wireless biological signal transmitter 10 and a wireless biological signal receiver 20.

The wireless biological signal transmitter 10 may measure a biological signal by being attached to the body or by approaching the body, and transmits the measured biological signal to the wireless biological signal receiver 20. More specifically, the wireless biological signal transmitter 10 may measure a biological signal caused by an electrical change, a biochemical change, physical motion of the body, and an environmental change by being attached to the body or by approaching the body, and transmits the measured biological signal to the wireless biological signal transmitter 20.

More specifically, the biological signal may include an electrical signal generated in the body, such as an electrocardiogram (ECG) obtained by recording an active current due to activity of the muscles of the heart, an electromyography (EMG) obtained by recording an active electrical potential of muscles, an electrooculogram (EOG) obtained by recording a biological electrical potential caused by eye movements, and an electroencephalogram (EEG) obtained by recording a current caused by activity of the brain. In addition, the biological signal may include an electrical signal related to an amount of body fat, an amount of muscle, and a skin hydration degree.

In addition, the biological signal may include an optically measured signal such as photoplethysmography (PPG) and an oxygen saturation degree. In addition, the biological signal may include a biological signal measured by using ultrasonic waves. In addition, the biological signal may include a biological signal measured by using radio frequency (RF) and terahertz band electromagnetic waves. In addition, the biological signal may include biochemical signal information such as body temperature, which is measured through conduction and radiation of heat, blood sugar, and anemia, information regarding movements, information regarding the personal environments of a user, such as the presence of ultraviolet rays, radioactive rays, biochemical and chemical components in the air, and the like.

The measured biological signal may be transmitted to the portable wireless biological signal transmitter 20 through wireless communication by using the RF band for the convenience of the user.

The wireless biological signal receiver 20 may receive a biological signal transmitted from the wireless biological signal transmitter 10, and calculates, stores, or determines the received biological signal. More specifically, the wireless biological signal receiver 20 may be installed in a portable device such as a mobile phone or a personal digital assistant (PDA) or installed externally on the portable device. Accordingly, the user can check their biological signal.

In this case, if the wireless biological signal receiver 20 is always maintained in a standby mode so as to continuously receive a biological signal from the wireless biological signal transmitter 10, power consumption is considerably large. Accordingly, the wireless biological signal receiver 20 is not suitable for a portable device such as a mobile phone or a PDA.

Accordingly, the wireless biological signal receiver 20 according to the current embodiment can change an operation mode of the wireless biological signal receiver 20 based on the properties of the biological signal transmitted from the wireless biological signal transmitter 10, as will be described in detail with reference to FIGS. 2 to 4.

Figure 2:
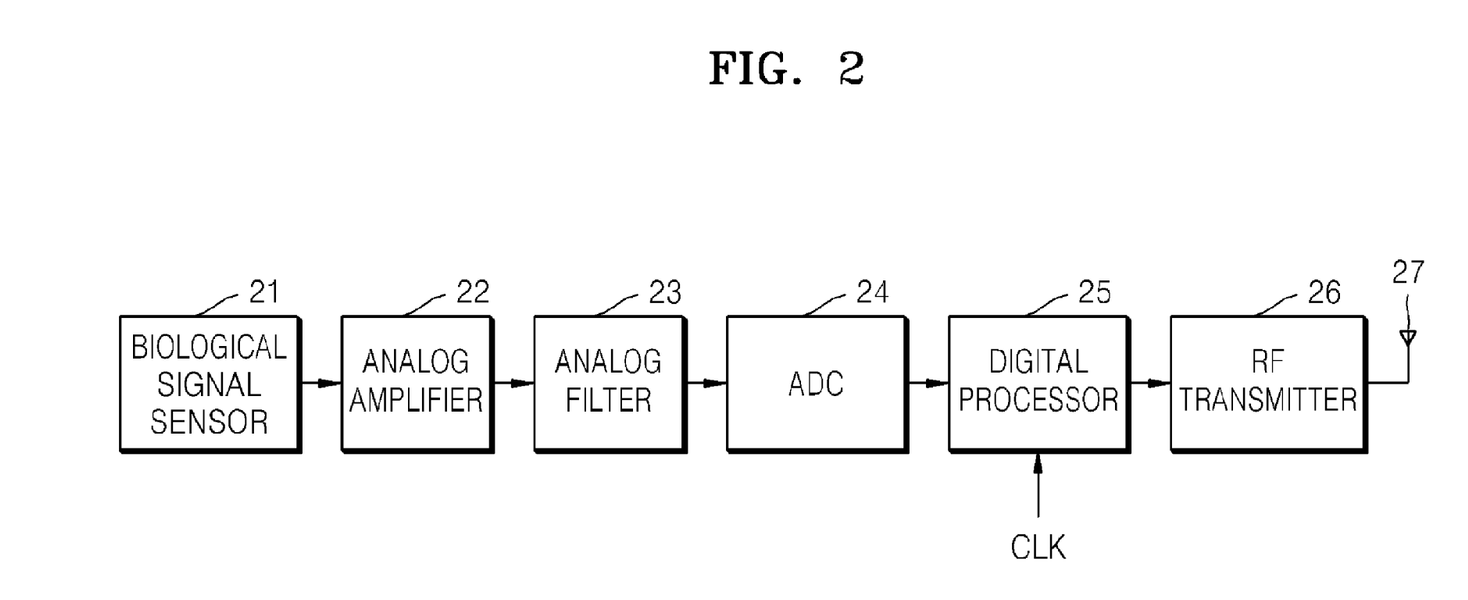
FIG. 2 is a block diagram illustrating a wireless biological signal transmitter included in the wireless system of FIG. 1.

FIG. 2 is a block diagram illustrating the wireless biological signal transmitter 10 included in the wireless system shown in FIG. 1.

Referring to FIG. 2, the wireless biological signal transmitter 10 may include a biological signal sensor 21, an analog amplifier 22, an analog filter 23, an analog-to-digital converter (ADC) 24, a digital processor 25, a RF transmitter 26, and an antenna 27.

The biological signal sensor 21 may measure a biological signal caused by an electrical change, a biochemical change physical motion of the body, and an environmental change by being attached to the body or by approaching the body. As described above, the biological signal may include an electrical signal from the ECG, the EMG, the GSR, the EEG, and the EOG, or a signal representing body temperature, a degree of motion, an amount of sweat, and the like. Here, the biological signal measured by the biological signal sensor 21 may be an analog signal.

The analog amplifier 22 may amplify the analog biological signal measured by the biological signal sensor 21. The analog filter 23 may filter only a predetermined region from a frequency band of the biological signal amplified by the analog amplifier 22. The ADC 24 may convert the analog signal filtered by the analog filter 23 into a digital signal.

The digital processor 25 may process the digital signal converted by the ADC 24 in order for the digital signal to be suitable for wireless transmission and constructs a data packet. More specifically, the digital processor 25 may process the converted digital signal. The wireless biological signal receiver 20 may construct the data packet constructed with a transmitter identifier (ID) for identifying the wireless biological signal transmitter 10, an index of transmitted data for indexing data transmitted from the wireless biological signal transmitter 10, a sampling frequency representing a sampling ratio of converting an analog biological signal into a digital signal, a transmission period for representing a temporal interval for transmitting each data to a receiver, error recovery data for obtaining normal data by correcting an error occurring in a transmission path of the data, and the like. Here, the digital processor 25 may be synchronized with a clock signal CLK that is received for each predetermined period.

The RF transmitter 26 may transmit the data packet that is output from the digital processor 25 as an RF signal. The antenna 27 may radiate the RF signal that is output from the RF transmitter 26 into the air.

Figure 3:
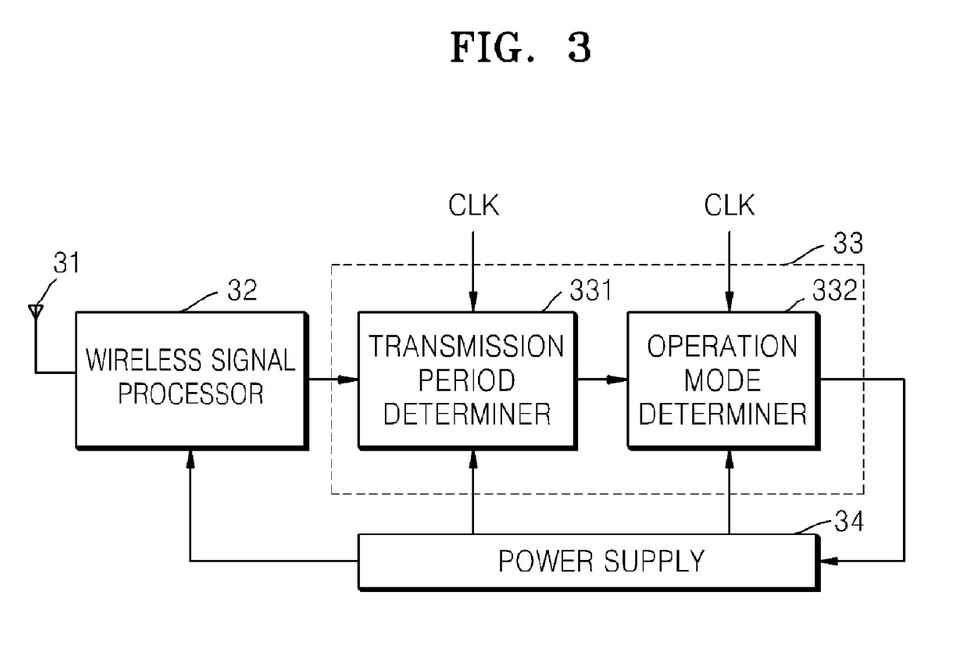
FIG. 3 is a block diagram illustrating a wireless biological signal receiver included in the wireless system of FIG. 1.

FIG. 3 is a block diagram illustrating the wireless biological signal receiver 20 included in the wireless system shown in FIG. 1.

Referring to FIG. 3, the wireless biological signal receiver 20 may include an antenna 31, a wireless signal processor 32, a data processor 33, and a power supply 34.

The antenna 31 may transmit an RF signal in the air to the wireless biological signal receiver 20. The wireless signal processor 32 may convert the RF signal received from the antenna 31 into data that can be processed by the data processor 33.

The data processor 33 may read and process the data that is output from the wireless signal processor 32 and determine an operation mode of the wireless biological signal receiver 20 based on a transmission period of the output data. In addition, the data processor 33 may be synchronized with a clock signal CLK that is received for each predetermined period. More specifically, the data processor 33 may include a transmission period determiner 331 and an operation mode determiner 332.

The transmission period determiner 331 may determine the transmission period of the data that is output from the wireless signal processor 32.

More specifically, the transmission period determiner 331 may receive data from the wireless signal processor 32 by two or more times and determine the transmission period based on a difference in time when data is received. For example, if the difference between a first time when data is received and a second time when data is received is ten seconds, the transmission period of data may be determined as ten seconds. In addition, the transmission period determiner 331 can synchronize an operation of receiving data by receiving data from the wireless signal processor 32 two or more times.

Then, the transmission period determiner 331 can correct an estimated value of the transmission period of the biological signal transmitted from the wireless biological signal transmitter 10 by periodically checking the transmission period. At this time, an operation mode of the wireless biological signal receiver 20 in a period for which the transmission period determiner 331 periodically checks a transmission period may be a transmission period measurement mode. The transmission period measurement mode may correspond to an active mode that is to be described later as a status in which it is possible to receive a biological signal.

Here, the transmission period determiner 331 can update the estimated value of the transmission period of the biological signal transmitted from the wireless biological signal transmitter 10 by using the transmission period periodically checked in the transmission period measurement mode based on an arithmetic or statistical method. Specifically, the estimated value of the transmission period that is to be updated through a correction may be an arithmetic mean of the transmission periods measured in the transmission period measurement mode or an optimal value induced through a statistical technique.

For example, it is assumed that a maximum error caused by inaccuracy of the transmission period of the wireless biological signal transmitter 10 is DT. The transmission period determiner 331 determines the transmission period as a first transmission period T−DT1 by initially receiving data two times. Then, the transmission period determiner 331 can estimate the first transmission period T−DT1 as the transmission period of the wireless biological signal transmitter 10. In addition, after receiving data n number of times, the transmission period determiner 331 can determine the transmission period as a second transmission period T+DT2 in the transmission period measurement mode. Here, DT1 and DT2 are less than DT.

The transmission period determiner 331 can correct a subsequent transmission period so as to obtain a third transmission period $T_{update}$. At this time, the third transmission period $T_{update}$ is an arithmetic mean of the first and second transmission periods T+DT1 and T+DT2 (that is, $T_{update}$=T+(−DT1+DT2)/2).

In addition, the transmission period determiner 331 may acquire additional information representing the transmission period included in the data that is output from the wireless signal processor 32 and determine the transmission period based on the acquired additional information. As described above, the data packet transmitted from the wireless biological signal transmitter 10 may include additional information representing the transmission period indicating a time interval at which data is transmitted to the wireless biological signal receiver 20. Accordingly, the transmission period determiner 331 can determine the transmission period of data based on the additional information.

In addition, the transmission period determiner 331 can determine the transmission period by selecting a value among a plurality of values corresponding to transmission periods of data with reference to a value according to a predetermined protocol. The wireless biological signal receiver 20 can previously set a plurality of values in correspondence with the transmission period of data to be received according to the predetermined protocol. Accordingly, the transmission period determiner 331 can determine the transmission period of data with reference to the value according to the predetermined protocol.

The operation mode determiner 332 may control the power supply 34 by setting the operation mode of the wireless biological signal receiver 20 to an active mode or a low-power mode based on the transmission period determined by the transmission period determiner 331. More specifically, the operation mode determiner 332 may receive data by setting the operation mode to an active mode for a predetermined time with respect to each determined transmission period. The operation mode may be changed from the active mode to the low-power mode after the predetermined time for each transmission period.

Here, in the active mode, it is possible to receive data transmitted from the wireless biological signal transmitter 10, and more specifically, power is supplied to hardware blocks included in the wireless biological signal receiver 20. For example, in the active mode, power is supplied to the wireless signal processor 32 included in the wireless biological signal receiver 20. Accordingly, in a case where the operation mode is set to the active mode, the operation mode determiner 332 operates so that the power supply 34 supplies power to the wireless signal processor 32.

In addition, in the low-power mode, it is impossible to receive data transmitted from the wireless biological signal transmitter 10, and more specifically, power is not supplied to some of the hardware blocks included in the wireless biological signal receiver 20, or minimum necessary power is supplied to the some of the hardware blocks. For example, in the low-power mode, power is not supplied to the wireless signal processor 32 included in the wireless biological signal receiver 20, or minimum power is supplied to the wireless signal processor 32. Accordingly, in a case where the operation mode is set to the low-power mode, the operation mode determiner 332 operates so that the power supply 34 does not supply power to the wireless signal processor 32 or supplies minimum power to the wireless signal processor 32. Thus, it is possible to considerably reduce power consumption of the wireless biological signal receiver 20 in the low-power mode.

Here, the predetermined time may include a first time interval that is set based on a time taken to set the operation mode to the active mode and an error caused by inaccuracy of the transmission period in the wireless biological signal transmitter 10 and a second time interval that is set based on an error caused by inaccuracy of the transmission period in the wireless biological signal transmitter 10, a delay time in a procedure of transmitting data, and a time of processing data.

In this case, the data processor 33 including the transmission period determiner 331 and the operation mode determiner 332 may be constructed with at least one of a main controller unit (MCU) for monitoring a biological signal and a central processing unit (CPU). Here, the MCU is a processor dedicated to controlling a specific system. In the present embodiment, the MCU is a processor dedicated to monitoring a biological signal. In this case, the MCU may be externally built separately from a CPU of a portable device such as a mobile phone, a PDA, or the like. Here, the CPU serves to decode data, perform arithmetic and logical operations, and process data. In the present embodiment, a program dedicated to monitoring a biological signal may be installed in the CPU of a portable device such as a mobile phone, a PDA, or the like.

As described above, since the wireless biological signal receiver 20 may be installed in or externally on a portable device, the data processor 33 may be constructed with one of the MCU and the CPU depending on whether the wireless biological signal receiver 20 is installed in or externally on the portable device. More specifically, if the wireless biological signal receiver 20 is installed in the portable device, it is possible for the CPU to process data that is output from the wireless signal processor 32 without a separate MCU. Accordingly, the data processor 33 may be constructed with only the CPU. In addition, if the wireless biological signal receiver 20 is installed externally on the portable device, the MCU can process data that is output from the wireless signal processor 32. Accordingly, the data processor 33 may be constructed with only the MCU.

The power supply 34 may supply power to the wireless signal processor 32 according to the operation mode determined by the operation mode determiner 332. More specifically, if the operation mode determined by the operation mode determiner 332 is the active mode, the power supply 34 supplies power to the wireless signal processor 32. If the determined operation mode is the low-power mode, the power supply 34 does not supply power to the wireless signal processor 32 or supplies minimum power to the wireless signal processor 32.

Figure 4:
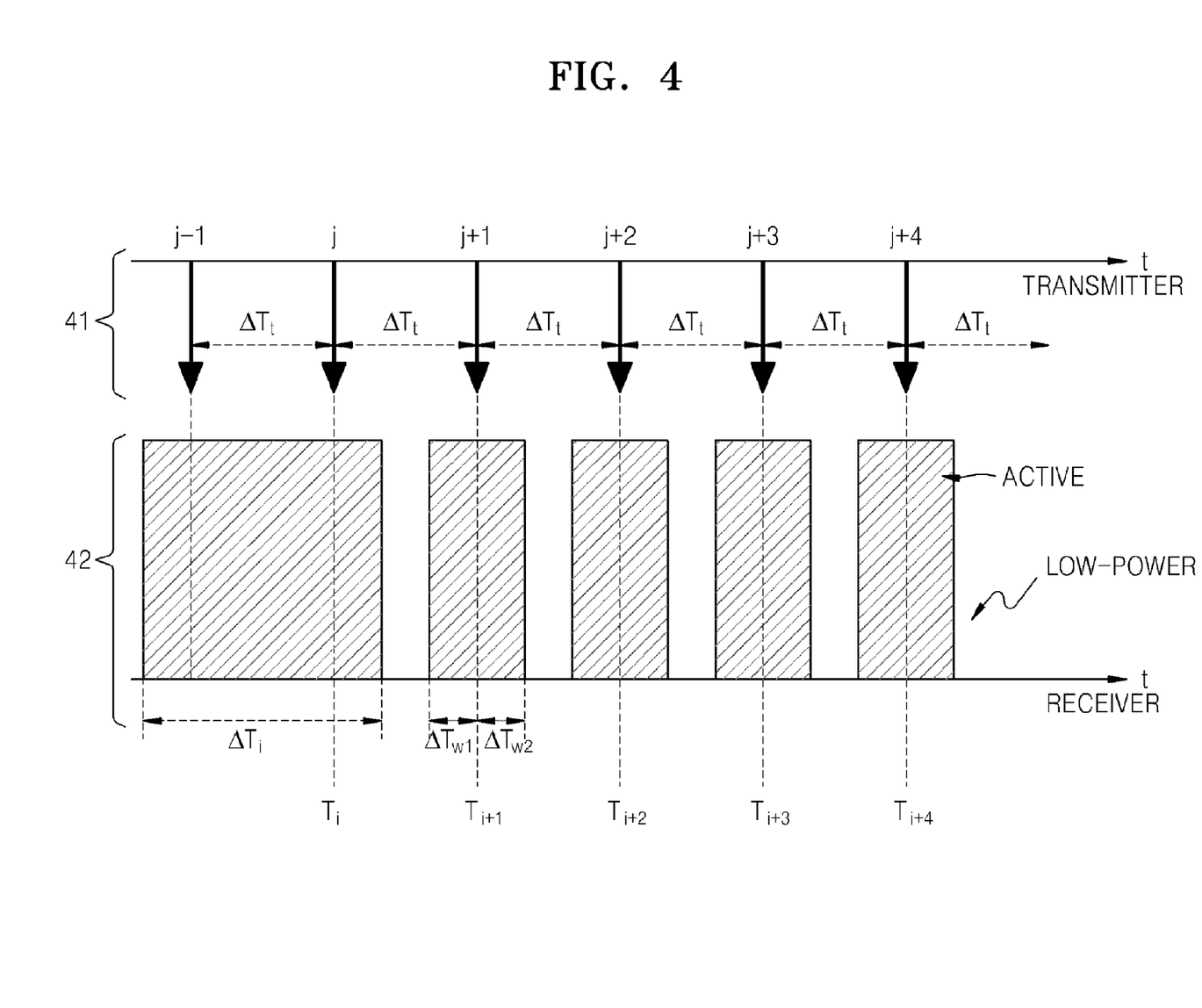
FIG. 4 is a timing diagram illustrating an operation of transmitting and receiving a biological signal, according to an embodiment of the present invention.

FIG. 4 is a timing diagram illustrating an operation of transmitting and receiving a biological signal, according to an embodiment of the present invention. Hereinafter, an operation of setting the operation mode by using the data processor 33 will be described in detail with reference to FIGS. 1 to 4.

Referring to FIG. 4, 41 represents transmission of data by using the wireless biological signal transmitter 10, and 42 represents an operation mode of the wireless biological signal receiver 20.

The wireless biological signal transmitter 10 may transmit (j−1)-th, j-th, (j+1)-th, (j+2)-th, (j+3)-th, and (j+4)-th data in a transmission period Tt. In addition, the wireless biological signal receiver 20 may receive data at times of $T_i$, $T_{i+1}$, $T_{i+2}$, $T_{i+3}$, and $T_{i+4}$ based on the transmission period Tt of data transmitted from the wireless biological signal transmitter 10, where j and i are natural numbers.

The wireless biological signal receiver 20 may set the operation mode to the active mode ACTIVE for a predetermined time interval $\Delta Ti$ where the predetermined time interval $\Delta Ti$ represents a time taken to receive data two or more times. Accordingly, it is possible to recognize the transmission period Tt of data and synchronize the transmission period Tt with the transmitted data by setting the operation mode to the active mode ACTIVE while receiving data two or more times. Here, in the active mode ACTIVE, it is possible to receive data, and power is supplied to each hardware block included in the wireless biological signal receiver 20.

After receiving j-th data from the wireless biological signal transmitter 10, the wireless biological signal receiver 20 may change the operation mode from the active mode ACTIVE to the low-power mode LOW-POWER, where the low-power mode may be an off mode or sleep mode in which it is impossible to receive data. More specifically, it is possible to reduce power consumption by not supplying a current to a predetermined number of hardware blocks such as the wireless signal processor 32 from among hardware blocks constituting the wireless biological signal receiver 20 in the low-power mode LOW-POWER according to settings.

The wireless biological signal receiver 20 may set the operation mode to the active mode ACTIVE for a predetermined time interval so as to receive the (j+1)-th data from the wireless biological signal transmitter 10 at a time of $T_{i+1}$, where the predetermined time interval includes first and second time intervals $\Delta T_{w1}$ and $\Delta T_{w2}$.

More specifically, the wireless biological signal receiver 20 may change the operation mode from the low-power mode LOW-POWER to the active mode ACTIVE before the first time interval $\Delta T_{w1}$ from when receiving (j+1)-th data from the wireless biological signal transmitter 10. In other words, a time when the wireless biological signal receiver 20 sets the operation mode to the active mode ACTIVE antecedes the calculated time corresponding to the transmission period Tt by the first time interval $\Delta T_{w1}$.

Here, the first time interval $\Delta T_{w1}$ represents an extra time obtained by considering a time taken to activate the wireless biological signal receiver 20, that is, a time taken to set the operation mode to the active mode ACTIVE, a time error between the wireless biological signal transmitter 10 and the wireless biological signal receiver 20, and the like. Specifically, the time error between the wireless biological signal transmitter 10 and the wireless biological signal receiver 20 may be caused by inaccuracy of the transmission period Tt of the biological signal that is transmitted from the wireless biological signal transmitter 10. For example, the wireless biological signal transmitter 10 may use a clock signal of which period is inaccurate for low-power driving. In this case, the transmission period is not the intended transmission period Tt but a value (Tsend+Tsend_error) including a time error Tsend_error. Accordingly, the first time interval $\Delta T_{w1}$ has to be set in consideration of the time error Tsend_error.

In addition, after the second time interval $\Delta T_{w2}$ from when receiving the (j+1)-th data from the wireless biological signal transmitter 10, the wireless biological signal receiver 20 may change the operation mode from the active mode ACTIVE to the low-power mode LOW-POWER. That is, a time when the wireless biological signal receiver 20 sets the operation mode to the low-power mode LOW-POWER follows a time corresponding to the transmission period by the second time interval $\Delta T_{w2}$.

Here, the second time interval $\Delta T_{w2}$ represents an extra time obtained by considering a time error between the wireless biological signal transmitter 10 and the wireless biological signal receiver 20, a transmission delay, a time taken to process data received by the wireless biological signal receiver 20, and the like. As described above, the time error between the wireless biological signal transmitter 10 and the wireless biological signal receiver 20 may be caused by inaccuracy of the transmission period Tt of the biological signal that is transmitted by the wireless biological signal transmitter 10.

The wireless biological signal receiver 20 may set the operation mode to the active mode ACTIVE for a predetermined time interval so as to receive (j+2)-th data from the wireless biological signal transmitter 10 at a time of $T_{i+2}$. Here, the predetermined time interval includes the first and second time intervals $\Delta T_{w1}$ and $\Delta T_{w2}$.

More specifically, the wireless biological signal receiver 20 may change the operation mode from the low-power mode LOW-POWER to the active mode ACTIVE before the first time interval $\Delta T_{w1}$ from when receiving the (j+2)-th data from the wireless biological signal transmitter 10. In addition, the wireless biological signal receiver 20 may change the operation mode from the active mode ACTIVE to the low-power mode LOW-POWER after the second time interval $\Delta T_{w2}$ from when receiving the (j+2)-th data from the wireless biological signal transmitter 10.

Similarly, the wireless biological signal receiver 20 may set the operation mode to the active mode ACTIVE for the predetermined time interval $\Delta T_{w1}+\Delta T_{w2}$ so as to receive (j+3)-th data from the wireless biological signal transmitter 10 at a time of $T_{i+3}$.

In addition, the wireless biological signal receiver 20 may set the operation mode to the active mode for the predetermined time interval $\Delta T_{w1}+\Delta T_{w2}$ so as to receive (j+4)-th data from the wireless biological signal transmitter 10 at a time of $T_{i+4}$.

As described above, the wireless biological signal receiver 20 may change the operation mode from the active mode ACTIVE to the low-power mode LOW-POWER or from the low-power mode LOW-POWER to the active mode ACTIVE based on the transmission period Tt of data that is transmitted from the wireless biological signal transmitter 10. That is, the wireless biological signal receiver 20 sets the operation mode to the active mode ACTIVE for only the predetermined time interval based on the transmission period Tt of data that is transmitted from the wireless biological signal transmitter 20 and sets the operation mode to the low-power mode LOW-POWER for the rest of the time.

Since the wireless biological signal transmitter 10 transmits a measured biological signal based on the transmission period Tt, the wireless biological signal receiver 20 acquires the transmission period Tt and periodically changes the operation mode from the active mode ACTIVE to the low-power mode LOW-POWER without determining whether there is received data, thereby considerably reducing power consumption of the wireless biological signal receiver 20.

Hereinafter, a reduction ratio of power consumption Ps for representing a reduction degree of a consumed current of the wireless biological signal receiver 20 according to the present embodiment with respect to a consumed current of a conventional receiver will be described with reference to Equation 1 as follows:

$$P_s = \frac{I_0 \Delta T_t + I_r(\Delta T_{w1} + \Delta T_{w2})}{(I_0 + I_r)\Delta T_t} =$$   [Equation 1]

-continued
$$\frac{I_0}{(I_0 + I_r)} + \frac{I_r}{I_0 + I_r}\frac{\Delta T_{w1} + \Delta T_{w2}}{\Delta T_t},$$

where the reduction ratio of power consumption Ps represents a ratio of power consumption in a case where the operation mode of the wireless biological signal receiver 20 is always set to the active mode ACTIVE with respect to power consumption in a case where the operation mode of the wireless biological signal receiver 20 is set to the active mode ACTIVE only when receiving data.

In addition, $I_0$ indicates a current consumed by the wireless biological signal receiver 20 when the operation mode of the wireless biological signal receiver 20 is set to the low-power mode LOW-POWER, and the $I_r$ indicates a current consumed by the wireless biological signal receiver 20 when the operation mode of the wireless biological signal receiver 20 is set to the active mode ACTIVE, where the consumed currents $I_0$ and $I_r$ are fixed values based on hardware structures.

In addition, $\Delta T_t$ indicates the transmission period of data that is transmitted from the wireless biological signal transmitter 10, and $\Delta T_{w1}+\Delta T_{w2}$ indicates a time when the operation mode of the wireless biological signal receiver 20 is the active mode ACTIVE for each transmission period of data. Here, $\Delta T_t$ and $\Delta T_{w1}+\Delta T_{w2}$ are not fixed based on hardware structures but are variable based on software settings.

For example, the current $I_0$ consumed by the wireless biological signal receiver 20 when the operation mode of the wireless biological signal receiver 20 is set to the low-power mode LOW-POWER is 3.9 mA, and the current $I_r$ consumed by the wireless biological signal receiver 20 when the operation mode of the wireless biological signal receiver 20 is set to the active mode ACTIVE is 19 mA. In addition, it is assumed that $\Delta T_t$ is 10 msec and $\Delta T_{w1}+\Delta T_{w2}$ is 1 msec. In this case, the reduction ratio of power consumption Ps is 25% (Ps=3.9/(3.9+19)+19/(3.9+19)*1/10=0.17+0.83*0.1=0.25).

Figure 5:
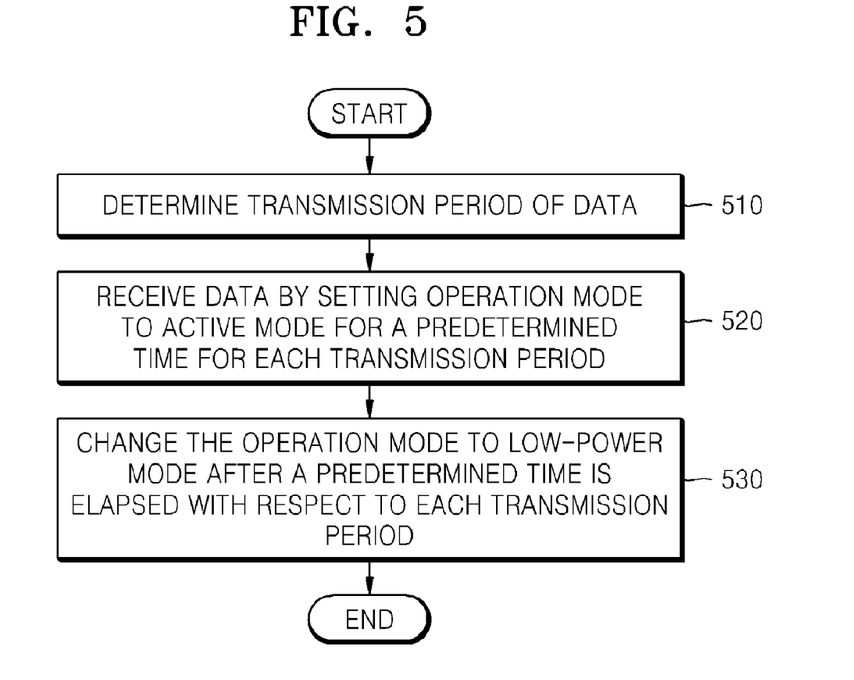
FIG. 5 is a flowchart of a method of wirelessly receiving data, according to an embodiment of the present invention.

FIG. 5 is a flowchart of a method of receiving wireless data, according to an embodiment of the present invention.

Referring to FIG. 5, the method of receiving wireless data according to the present embodiment includes operations sequentially performed by the wireless biological signal receiver 20 of FIG. 3. Accordingly, although the aforementioned description on the wireless biological signal receiver 20 is omitted, the description also applies to the method of receiving wireless data according to the present embodiment.

In operation 510, a transmission period of externally received data is determined.

In operation 520, data is received by setting an operation mode to an active mode in which it is possible to receive data for a predetermined time for each determined transmission period. More specifically, the operation mode may be set to the active mode at a time that antecedes a time corresponding to the determined transmission period by a first time interval.

In operation 530, the operation mode is changed from the active mode to a low-power mode in which it is impossible to receive data, after a predetermined time is elapsed with respect to each transmission period. More specifically, it is possible to change the operation mode from the active mode to the low-power mode at a time that follows a time corresponding to the determined transmission period by a second time interval.

Figure 6:
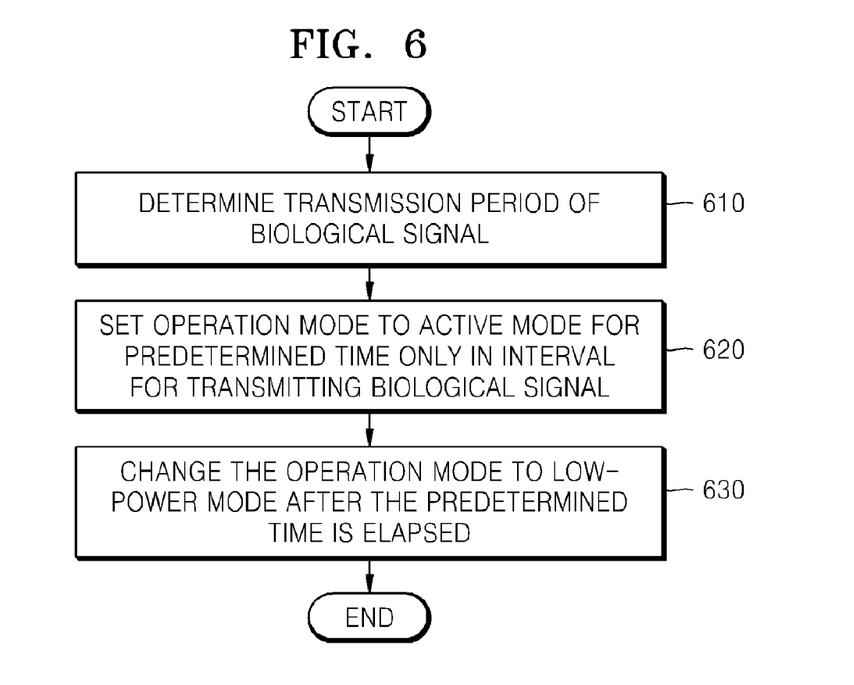
FIG. 6 is a flowchart of a method of wirelessly receiving a biological signal, according to an embodiment of the present invention.

FIG. 6 is a flowchart of a method of wirelessly receiving a biological signal, according to an embodiment of the present invention.

Referring to FIG. 6, the method of wirelessly receiving a biological signal according to the present embodiment includes operations sequentially performed by the wireless biological signal receiver 20 of FIG. 3. Accordingly, although aforementioned description on the wireless biological signal receiver 20 is omitted, the description also applies to the method of wirelessly receiving biological signal according to the present embodiment.

In operation 610, a transmission period of the biological signal is determined by receiving the wirelessly transmitted biological signal.

In operation 620, an operation mode is set to an active mode in which it is possible to receive the biological signal for a predetermined time only in an interval for which the biological signal is transmitted. More specifically, the operation mode may be set to the active mode at a time that antecedes a time corresponding to the determined transmission period by a first time interval.

In operation 630, after the predetermined time, the operation mode is changed from the active mode to a low-power mode in which it is impossible to receive the biological signal. More specifically, it is possible to change the operation mode from the active mode to the low-power mode at a time that follows a time corresponding to the determined transmission period by a second time interval.

In addition to the above described embodiments, embodiments of the present invention can also be implemented through computer readable code/instructions in/on a medium, e.g., a computer readable medium, to control at least one processing element to implement any above described embodiment. The medium can correspond to any medium/media permitting the storing and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as carrier waves, as well as through the Internet, for example. Thus, the medium may further be a signal, such as a resultant signal or bitstream, according to embodiments of the present invention. The media may also be a distributed network, so that the computer readable code is stored/transferred and executed in a distributed fashion. Still further, as only an example, the processing element could include a processor or a computer processor, and processing elements may be distributed and/or included in a single device.

As described above, according to one or more embodiments of the embodiment, it is possible to considerably reduce power consumption of a receiver by determining a transmission period of an externally received biological signal, setting an operation mode of the wireless biological signal receiver to an active mode in which it is possible to receive the biological signal for a predetermined time for each determined transmission period, receiving the biological signal, and changing the operation mode from the active mode to a low-power mode in which it is impossible to receive the biological signal, after the predetermined time is elapsed with respect to each determined transmission period.

While aspects of the present invention has been particularly shown and described with reference to differing embodiments thereof, it should be understood that these exemplary embodiments should be considered in a descriptive sense only and not for purposes of limitation. Any narrowing or broadening of functionality or capability of an aspect in one embodiment should not considered as a respective broadening or narrowing of similar features in a different embodiment, i.e., descriptions of features or aspects within each embodiment should typically be considered as available for other similar features or aspects in the remaining embodiments.

Thus, although a few embodiments have been shown and described, it would be appreciated by those skilled in the art that changes may be made in these embodiments without departing from the principles and spirit of the invention, the scope of which is defined in the claims and their equivalents.

What is claimed is:

1. A method of receiving a biological signal by using a wireless biological signal receiver, the method comprising:
   determining a transmission period of an externally received biological signal;
   setting an operation mode of the wireless biological signal receiver to an active mode in which it is possible to receive the biological signal for a predetermined time for each determined transmission period and receiving the biological signal; and
   changing the operation mode from the active mode to a low-power mode in which it is impossible to receive the biological signal, after the predetermined time is elapsed with respect to each determined transmission period.

2. The method of claim 1, wherein the determining of the transmission period includes:
   externally receiving the biological signal two or more times; and
   determining the transmission period based on a difference in time when each biological signal is received.

3. The method of claim 2, wherein the determining of the transmission period further includes maintaining the active mode in which it is possible to receive the biological signal as the operation mode.

4. The method of claim 2, wherein the determining of the transmission period further includes modifying the transmission period based on an arithmetic or statistical method by periodically checking the transmission period.

5. The method of claim 1, wherein the biological signal includes at least one of an electrical signal generated in the body, an electrical signal measured by applying electricity to the human body, an optically measured signal, a signal measured by using ultrasonic waves, a signal measured by using electromagnetic waves, information regarding body temperature measured through conduction of heat, biochemical signal information, body movement information, and information regarding personal environments.

6. The method of claim 1, wherein the determining of the transmission period includes:
   acquiring additional information representing the transmission period included in the received biological signal; and
   determining the transmission period based on the acquired additional information.

7. The method of claim 1, wherein in the determining of the transmission period, the transmission period is determined by selecting one from among a plurality of values corresponding to the transmission period of the biological signal with reference to a value according to a predetermined protocol.

8. The method of claim 1, wherein the predetermined time includes:
   a first time interval which is set based on a time taken to set the operation mode to the active mode and an error caused by inaccuracy in the transmission period of a transmitter that transmits the biological signal; and
   a second time interval which is set based on an error caused by the inaccuracy in the transmission period of the transmitter, a delay time in a procedure of transmitting the biological signal, and a time for processing the biological signal.

9. The method of claim 8,
wherein in the receiving of the biological signal by setting the operation mode to the active mode, the biological signal is received by setting the operation mode to the active mode at a time that antecedes a time corresponding to the determined transmission period by the first time interval, and
wherein in the changing of the operation mode to the low-power mode, the operation mode is changed from the active mode to the low-power mode at a time that follows a time corresponding to the determined transmission period by the second time interval.

10. A computer-readable medium encoded with a computer program configured to cause a processor to execute a method of wirelessly receiving a biological signal by using a wireless biological signal receiver, the method comprising:
  determining a transmission period of an externally received biological signal;
  setting an operation mode of the wireless biological signal receiver to an active mode in which it is possible to receive the biological signal for a predetermined time for each determined transmission period and receiving the biological signal; and
  changing the operation mode from the active mode to a low-power mode in which it is impossible to receive the biological signal, after the predetermined time is elapsed with respect to each determined transmission period.

11. A wireless biological signal receiver comprising:
  a transmission period determiner to determine a transmission period of an externally received biological signal; and
  an operation mode determiner to set an operation mode of the wireless biological signal receiver to an active mode in which it is possible to receive the biological signal for a predetermined time for each determined transmission period, receiving the biological signal, and changing the operation mode from the active mode to a low-power mode in which it is impossible to receive the biological signal, after the predetermined time is elapsed with respect to each determined transmission period.

12. The wireless biological signal receiver of claim 11, wherein the transmission period determiner externally receives the biological signal two or more times and determines the transmission period based on a difference in time when each biological signal is received.

13. The wireless biological signal receiver of claim 11, wherein the transmission period determiner acquires additional information representing the transmission period included in the received biological signal and determines the transmission period based on the acquired additional information.

14. The wireless biological signal receiver of claim 11, wherein the transmission period determiner determines the transmission period by selecting one from among a plurality of values corresponding to the transmission period of the biological signal with reference to a value according to a predetermined protocol.

15. The wireless biological signal receiver of claim 11, wherein the predetermined time includes:
  a first time interval which is set based on a time taken to set the operation mode to the active mode and an error caused by inaccuracy in the transmission period of a transmitter that transmits the biological signal; and
  a second time interval which is set based on an error caused by the inaccuracy in the transmission period of the transmitter, a delay time in a procedure of transmitting the biological signal, and a time for processing the biological signal.

16. The wireless biological signal receiver of claim 11, further comprising a clock to supply a clock signal to the transmission period determiner and the operation mode determiner in a predetermined period.

17. The wireless biological signal receiver of claim 11, further comprising an RF signal processor to convert an RF signal into a signal to be processed by the transmission period determiner and the operation mode determiner, wherein the biological signal is the RF signal.

18. The wireless biological signal receiver of claim 17, further comprising a power supply to supply power to the RF signal processor according to the operation mode that is determined by the operation mode determiner.

* * * * *